United States Patent [19]

Rieder

[11] 4,016,420

[45] Apr. 5, 1977

[54] PRECESSION-TYPE X-RAY DIFFRACTION CAMERA

[75] Inventor: Milan Rieder, Prague, Czechoslovakia

[73] Assignee: Dekanat Prirodovedecke Fakulty University Karlovy, Prague, Czechoslovakia

[22] Filed: May 30, 1975

[21] Appl. No.: 582,343

[52] U.S. Cl. .................................. 250/277 CH
[51] Int. Cl.² .................................. G01M 23/20
[58] Field of Search ............ 250/277 CH, 278, 279, 250/453, 454

[56] References Cited

UNITED STATES PATENTS

| | | | |
|---|---|---|---|
| 2,540,821 | 2/1951 | Harker | 250/277 CH |
| 2,958,776 | 11/1960 | Jones et al. | 250/277 CH |
| 3,728,541 | 4/1973 | Rabinovich et al. | 250/277 CH |

*Primary Examiner*—Alfred E. Smith
*Assistant Examiner*—Bruce C. Anderson

[57] ABSTRACT

A precession-type X-ray diffraction camera is provided with facilities for extending the range of information obtained by the crystal diffraction patterns on film without the necessity of additional handling of the crystal. The crystal holder is supported for movement within a circumferential groove of a circular segment that is attached to a support member carried in a two-axis mount. The circular segment is oriented in a plane that is perpendicular to such support member and which is parallel to an elongated element defining the axis of precession of the camera. The movement of the crystal holder in the groove permits an additional degree of variation of the crystal orientation with respect to the incoming collimated X-rays, without disturbing the nominal position of the crystal at the intersection of the collimation axis with the respective axes of the mount.

9 Claims, 3 Drawing Figures

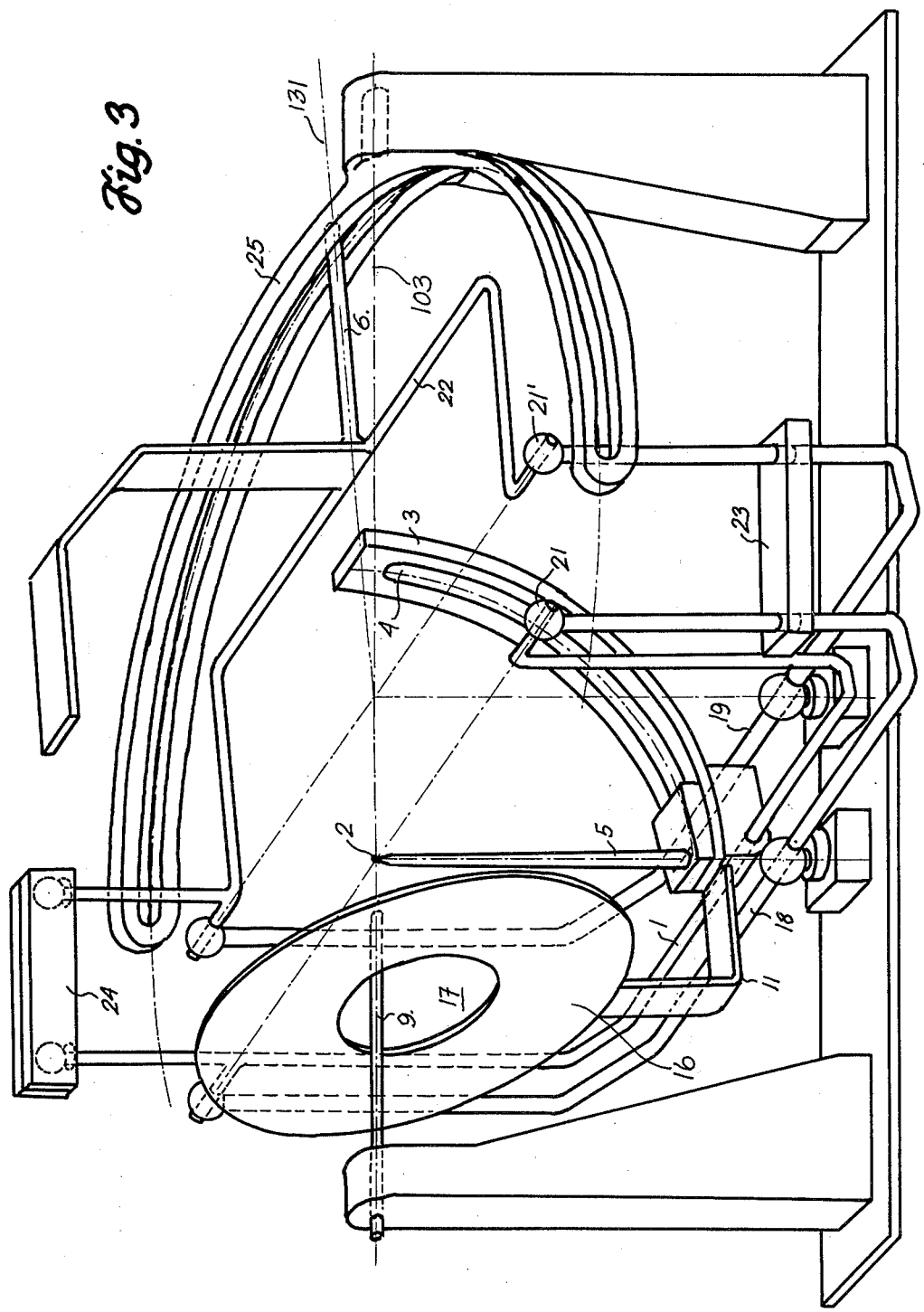

PRECESSION-TYPE X-RAY DIFFRACTION CAMERA

BACKGROUND OF THE INVENTION

Existing precession-type cameras for taking X-ray diffraction pictures of a crystal include a two-axis mount wherein a pair of frames are journalled for rotation about ganged vertical axes and are connected to a pair of support members that are journalled for rotation about ganged horizontal axes that respectively intersect the ganged vertical axes. The resultant mount is in turn supported for precession about a principal collimation axis of the camera, with the precession angle being determined by the deviation, from such collimation axis, of an elongated element affixed to the mount and extending perpendicular to its horizontal axes.

The crystal whose diffraction pattern is to be recorded is disposed in a holder at the intersection of the collimation axis and the junction of the vertical and horizontal axes in one portion of the mount. In existing designs of this type, the crystal holder, with an associated goniometer head, is fixedly connected to the associated support member of the mount. It has been found that under such circumstances, it is impractical, with a single fixing of the crystal within the camera, to take diffraction pictures in the front-reflection region at precession angles greater than 45 degrees. Moreover, in such systems, the only reciprocal nets that can be recorded are those which are parallel to the main axis of the goniometer head and thereby of the crystal holder.

SUMMARY OF THE INVENTION

The improvements provided by the present invention are effective to increase the information content which can be recorded by taking X-ray diffraction pictures of a crystal without the necessity of additional handling of the crystal.

In an illustrative embodiment, a circular segment is connected to the crystal holder support member and is provided with a 90 degree circumferential groove therein. Such segment is oriented in a plane which is perpendicular to such support member and parallel to the precession axis of the system mount. The crystal holder, rather than being fixedly connected to the associated support member, is instead supported for circumferential movement in the groove of the segment. The resultant increase in the degrees of orientation of the crystal relative to the incoming X-rays make it possible to record a plurality of systems of reciprocal nets, thereby enabling a much more versatile application of the camera.

The camera may also be provided with two planar film holders, the first of which is disposed intermediate the X-ray tube and the crystal along the collimation axis. The first film holder may be connected to the portion of the two-axis mount associated with the precession element, and the second may be connected to the crystal holder support member. Both film holders make right angles with the precession ones.

In the former case, a screen is suitably supported by the crystal holder support member intermediate the first film holder and the crystal, while in the latter case the second film holder is directly mounted on the crystal holder support member, and is advantageously formed as an annulus having a central opening through which the collimator extends.

BRIEF DESCRIPTION OF THE DRAWING

The invention is further set forth in the following detailed description taken in conjunction with the appended drawing, in which:

FIG. 3 is a perspective view, similar to FIG. 1, of a second embodiment of an X-ray diffraction camera constructed in accordance with the invention.

DETAILED DESCRIPTION

Figure 1:
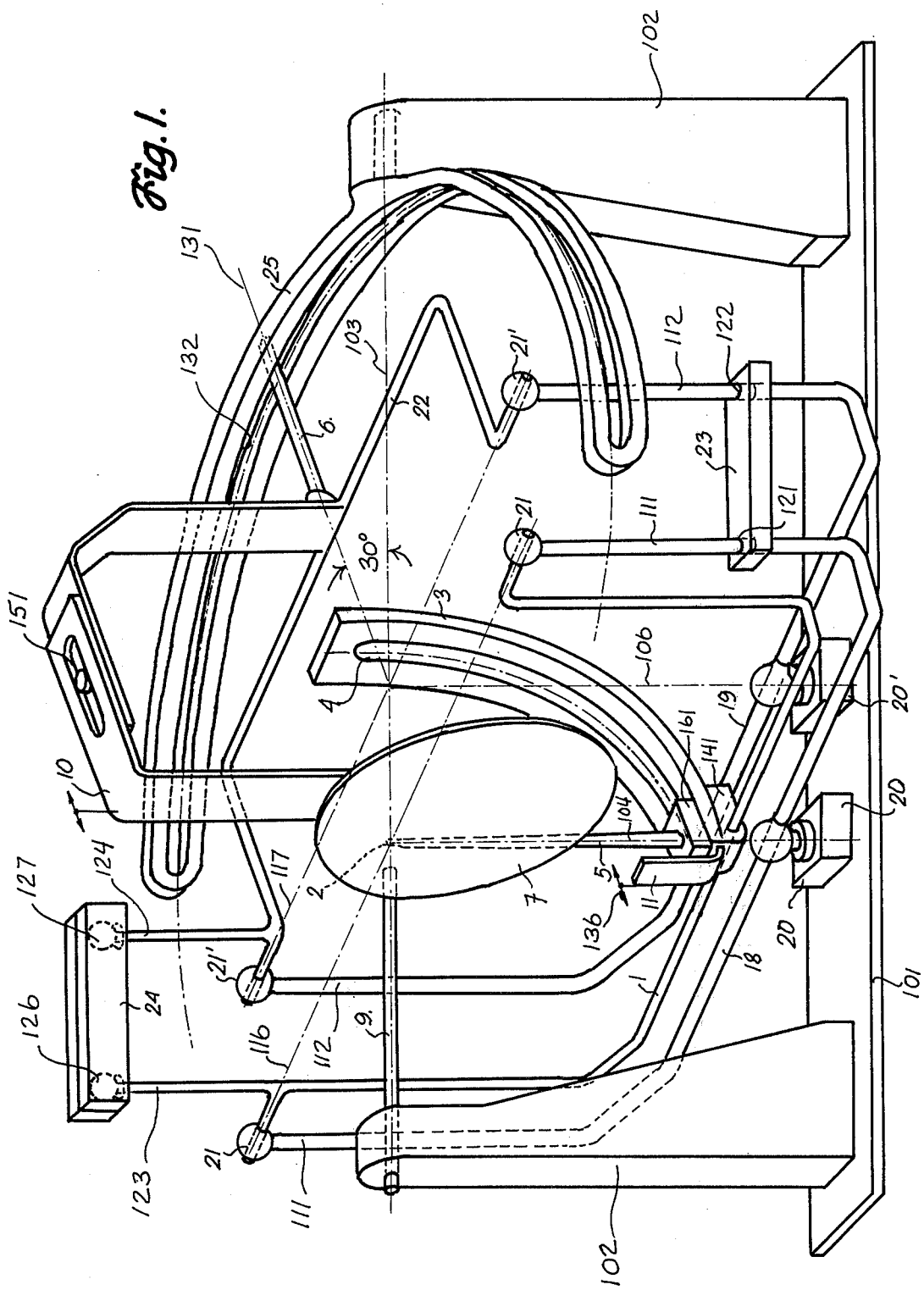
FIG. 1 is a perspective view of a first embodiment of an X-ray diffraction camera constructed in accordance with the invention.

Referring now to the drawing, FIG. 1 illustrates a first embodiment of the invention in the form of a back-reflection, precession-type X-ray diffraction camera which is adapted for taking pictures of a reciprocal net of the crystal at a precession angle of 30°. As indicated below, a screen having an annular, X-ray-transparent opening can be employed to isolate the diffraction cone corresponding to a reciprocal net at such precession angle, which cone can be recorded on a suitable film in the form of a circle.

The arrangement of FIG. 1 includes a base 101 on which there are mounted two spaced pedestals 102—102.

The pedestals 102—102 are aligned along a main horizontal collimation axis 103 of the camera.

X-rays from a suitable tube (not shown) are directed along a collimating element 9 to converge on a crystal 2, whose X-ray diffraction pattern is to be recorded on a suitable film carried by a first planar film holder 7.

The orientation of the crystal 2 with respect to the incoming collimates X-rays may be suitably varied in a basic three-axis arrangement wherein a pair of frame members 18 and 19 are journalled for rotation around a pair of vertical axes 104, 106, which are defined by a pair of bearings 20, 20' supported on the base 101. The respective frames 18 and 19 are provided with upstanding portions 111 — 111 and 112 — 112, respectively, the upper ends of which support a pair of bearings 21—21 and 21'—21'. The bearings 21, 21' define a pair of horizontal axes 116, 117. Within the bearings 21, 21' are journalled a crystal holder support member 1 and an auxiliary support member 22, which in the arrangement of FIG. 1 carries the film holder 7 via an adjustable, U-shaped arm 10.

The upstanding portions 111, 112 of the frames 18, 19 are respectively ganged together by means of a member 23 having a pair of vertical joints 121, 122. In like manner, upwardly extending extensions 123, 124 of the crystal holder support member 1 and the auxiliary support member 22 are ganged together by means of a member 24, which contains a pair of ball joints 126, 127. The vertical axis 104 and the horizontal axis 116 associated with the crystal support member intersect on the collimation axis 103. In like manner, the vertical axis 106 and the horizontal axis 117 associated with the film holder support member 22 also intersect on the collimation axis 103.

The two-axis mount defined by the interconnected frames 18, 19 and support members 1, 22 are adapted for precession about the collimation axis 103. For this purpose, an elongated element 6 extends from the support member 22 in a direction perpendicular to the associated horizontal axis 117 to define a precession axis 131. The element 6 extends through and is captured within a circumferential groove 132 disposed in a circular segment 25, which is supported on the pedestal 102 for rotation about the collimation axis 103. Such two-axis mount precesses about the axis 103 at a selectable angle determined by a pre-set deviation of the axis 131 with respect to the axis 103.

The crystal 2 is mounted on a holder 5, which may include a suitable goniometer head, at the intersection of the collimation axis 103 and the junction of the horizontal and vertical axes 116, 104 associated with the crystal holder support member. The crystal is adapted to reflect a characteristic X-ray diffraction pattern in the direction toward the left as shown in the drawing upon being bombarded with collimated X-rays via the collimator 9. The diffraction pattern is recorded on a suitable film carried by the first film holder 7. In order to isolate the characteristic diffraction cone associated with a reciprocal net at a precession angle of 30° as shown, a screen plate 12 (FIG. 2) may be interposed between the crystal 2 and the first film holder 7, such plate 12 having integral therewith a screen 13, 13' defining an X-ray transparent annulus 15. Such annulus 15, interposed in the path of the scattered X-rays, results in a characteristic recording of a circular plot 26 on the film of the first film holder 7 as the two-axis mount precesses about the collimation axis 103 (FIG. 1). The screen plate 12 is supported on an L-shaped arm 11 associated with the crystal holder support member 1. In particular, the member 11 is mounted for movement along the precession axis 131 in a casing 141 attached to the crystal holder support member 1.

Figure 2:
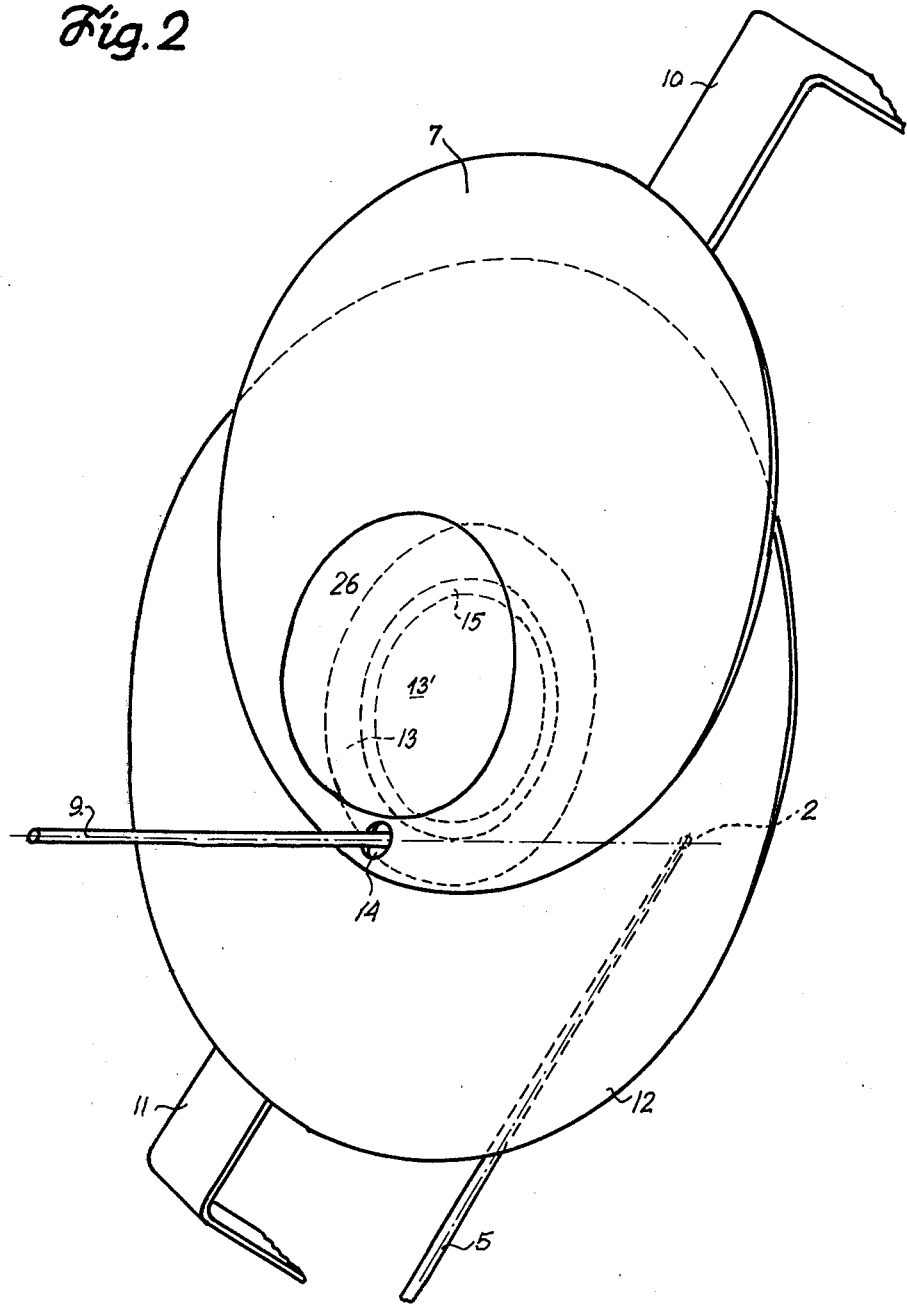
FIG. 2 is a perspective view of a screen arrangement suitable for use in the arrangement of FIG. 1.

As indicated in FIG. 2, the collimator 9 extends through an opening 14 in the screen member 13, such opening being disposed radially outward of the annulus 15. The screen 13 rotates with the screen plate 12 about an axis normal to the screen plate 12, such rotation being effective by relative motion of the screen plate 12 and the collimator 9. The radial disposition of the opening 14 is appropriate where the apex angle of the diffraction cone is smaller than the precession angle (illustratively 30 degrees). In such a case, the annular space 15 extends 360 degrees around the axis of the plate 12, and the internal portion 13' of the screen is maintained centralized with respect to the outer portion 13 by means of a suitable solid X-ray transparent material. In the case where the apex angle of the diffraction cone is equal to the precession angle, the opening 14 is radially coincident with the annulus 15, which would then extend less than 360°. If the apex angle of the diffraction cone is larger than the precession angle, the guiding opening 14 would be disposed radially inwardly of the annulus 15. As indicated above, the L-shaped arm 11 is effective to set the distance between the screen member 12 and the crystal 2. In like manner, a slotted portion 151 of the U-shaped arm 10 is effective to set the distance, along the precession axis 131, between the intersection of axes 103, 106, 117 and 131 and the first film holder 7.

In the arrangement of FIG. 1, a 360° precession of the axis 131 about the collimation axis 103 is precluded because of the resultant interference between the arm 10 and the collimator 9. Accordingly, the precession motion will take on an oscillatory nature, with the difference between the total oscillatory movement and 360 degrees being determined by the diameter of the collimator 9 and the width of the arm 10.

In accordance with the invention, the crystal 2 can be given an additional degree of freedom with respect to the collimation axis 103, and thereby can be made to yield an additional quantity of X-ray diffraction information, by providing in the arrangement of FIG. 1 an additional circular segment 3 having a 90° circumferential slot 4. The segment 3 is affixed on the crystal holder support member 1, and is oriented in a plane which is perpendicular to the support member 1 and parallel to the precession axis 131. A base block 161 of the crystal holder 5 is supported for circumferential movement within the groove 4 of the segment 3, whereby the orientation of the crystal 2 can be effectively varied without changing the positioning of the crystal 2 at the intersection of the axes 103, 104 and 116.

The arrangement of FIG. 3, in which portions thereof corresponding to FIG. 1 have been given the same reference numerals, the improved diffraction camera of the invention is provided with a modified second film holder arrangement suitable for use of the so-called "cone axis" technique. In this arrangement, a circular second film holder 16 having a central opening 17 traversed by the collimator 9 is supported directly on the L-shaped arm 11, to which the screen of the arrangement of FIG. 2 was attached. With such illustrated mounting of the second film holder 16, the first film holder 7 and the U-shaped arm are decoupled from the auxiliary support member 22, whereby a full 360 degree precessional movement of the axis 131 about the axis 103 can take place, since no danger of interference exists between the arm 10 and the collimator 9.

In the "cone axis technique," the ring-shaped second film holder 16 of FIG. 3 is maintained fixed in position with respect to the diffraction cones associated with the different reciprocal nets of the crystal. The diffraction traces that correspond to the respective sets of reciprocal nets perpendicular to the precession axis 131 are manifested on the film as concentric circles.

In the foregoing, the invention has been described in connection with illustrative embodiments thereof. Many variations and modifications will now occur to those skilled in the art. It is accordingly desired that the scope of the appended claims not be limited to the specific disclosure herein contained.

What is claimed is:

1. In a precession camera for taking X-ray diffraction pictures of a crystal, a collimator for directing X-rays along a first fixed horizontal axis, first and second frames individually supported for rotation about second and third ganged vertical axes each intersecting the first axis, first and second support members individually connected to the first and second frames for rotation about fourth and fifth ganged horizontal axes individually intersecting the second and third axes and each intersecting the first axis, the interconnected frames and support members defining a two-axis sub-system, a crystal holder for supporting the crystal at the intersection of the first, third and fifth axes, an elongated element coupled to the first support member and extending perpendicular to the fourth axis to define a sixth axis, a first planar film holder supported along the first axis in the path of the X-rays and disposed perpendicular to the sixth axis, the collimator extending through the plane of the film holder, means including the element for precessing the sub-system about the first axis at a selectable angle determined by the deviation of the sixth axis from the first axis, a first circular segment connected to the second support member and having a first 90° circumferential groove therein, the first segment being oriented in a plane perpendicular to the second support member and parallel to the sixth axis, and means supporting the crystal holder for circumferential movement in the first groove.

2. A camera as defined in claim 1, in which the precessing means comprises a second circular segment supported for rotation about the first axis, the second segment having a second circumferential groove for receiving the element.

3. A camera as defined in claim 1, further comprising means aligned with the sixth axis for connecting the film holder to the first support member.

4. A camera as defined in claim 3, in which the connecting means comprises means for adjusting the distance along the sixth axis between the first film holder and the intersection of the first, second, fourth and sixth axes.

5. A camera as defined in claim 4, further comprising a planar screen perpendicular to the sixth axis and connected to the second support member intermediate the crystal and the film holder, the screen being generally opaque to X-rays, the collimator extending through the plane of the screen.

6. A camera as defined in claim 5, in which the screen includes an annular segment transparent to X-rays.

7. A camera as defined in claim 1, further comprising a second planar film holder, and means for connecting the second film holder to the second support member so that the second film holder is perpendicular to the sixth axis.

8. A camera as defined in claim 7, in which the connecting means includes means for adjusting the distance along the sixth axis between the crystal and the second film holder.

9. A camera as defined in claim 8, in which the second film holder is in the form of an annulus having a central opening through which the collimator extends.

* * * * *